United States Patent [19]

Colombo et al.

[11] Patent Number: 4,839,177
[45] Date of Patent: Jun. 13, 1989

[54] SYSTEM FOR THE CONTROLLED-RATE RELEASE OF ACTIVE SUBSTANCES

[75] Inventors: Paolo Colombo; Aldo La Manna, both of Pavia; Ubaldo Conte, Busto Arsizio, all of Italy

[73] Assignee: Jagotec AG, Hergiswill, Switzerland

[21] Appl. No.: 939,810

[22] Filed: Dec. 9, 1986

[30] Foreign Application Priority Data

Dec. 20, 1985 [IT] Italy ............................. 23321 A/85

[51] Int. Cl.$^4$ ............................................. A61K 9/32
[52] U.S. Cl. ................................. 424/482; 424/470; 424/497; 427/3
[58] Field of Search ............... 424/419, 443, 485, 486, 424/494, 470, 472, 482, 486, 501, 497; 427/3

[56] References Cited

U.S. PATENT DOCUMENTS

| | | | |
|---|---|---|---|
| 3,634,584 | 1/1972 | Poole ............................. | 424/471 X |
| 4,122,157 | 10/1978 | Huber ............................ | 424/472 |
| 4,140,755 | 2/1979 | Sheth et al. ..................... | 424/472 |
| 4,389,393 | 6/1983 | Schor et al. ..................... | 424/362 X |
| 4,432,966 | 2/1984 | Zeitoun et al. ................... | 424/471 X |
| 4,483,846 | 11/1984 | Koida et al. ..................... | 424/443 X |

FOREIGN PATENT DOCUMENTS 1022171 3/1966 United Kingdom .
1346609 2/1974 United Kingdom .

Primary Examiner—Michael Lusignan
Attorney, Agent, or Firm—Parkhurst, Oliff & Berridge

[57] ABSTRACT

A system for the controlled-rate release of active substances, consisting of:

(a) a deposit-core comprising the active substance and having defined geometric form;
(b) a support-platform applied to said deposit-core.

Said deposit-core contains, mixed with the active substance, a polymeric material having a high degree of swelling on contact with water or aqueous liquids, a gellable polymeric material, said polymeric materials being replaceable by a single polymeric material having both swelling and gelling properties, and other adjuvants able to provide the mixture with suitable characteristics for its compression and for its intake of water.

Said support-platform consists of a polymeric material insoluble in aqueous liquids and partially coating said deposit-core.

The intensity and duration of the swelling force of said polymeric material with a high degree of swelling constitutes the primary factor in controlling the release of the active substance.

25 Claims, 1 Drawing Sheet

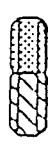

SYSTEM FOR THE CONTROLLED-RATE RELEASE OF ACTIVE SUBSTANCES

This invention relates to a system able to release a contained active substance at a practically constant controlled rate into a fluid able to cause swelling of the deposit-core containing the active substance.

The active substance to be released can consist of pesticides, herbicides, fertilisers, room deodorants, medicaments and generally any type of substance which requires to be released at a controlled rate into an aqueous fluid.

Releasing an active substance at a practically constant rate from the system containing it enables accuracy and selectivity of action, administration reduction and optimum overall utilisation to be obtained for the active substance, with both practical and economical advantages.

For example, in agriculture an insecticide or parasiticide activity can be obtained for prolonged time periods programmable in relation both to the specific requirements and to the existing or predicted moisture and temperature conditions.

Systems for the controlled release of active substances are used in many sectors of application, as stated heretofore, however the sector in which this requirement is particularly felt is that involving the administration of medicaments both in human and in veterinary therapy.

In this respect, particularly in the treatment of chronic illnesses with active substances having a short half-life, the therapy requires very frequent administration (4–5 times per day), which is poorly supported by the patient and can become aleatory in its results.

To obtain greater posological simplicity and increase the acceptability of the administration scheme by the patient, so-called "delayed-action" pharmaceutical forms which can require only one administration per day have been conceived and used in therapy.

The most advanced of these forms is known as a "therapeutic system", and consists of the following essential parts:
(a) the medicament,
(b) a release module comprising a deposit of the medicament, the control element, the energy source and the release surface,
(c) a platform for keeping the system in seat,
(d) the therapeutic programme The studies and implementations of these systems have mainly involved active principles which are soluble or very soluble in water, and are transferred by the pharmaceutical forms in which they are carried after dissolution. In these implementations, the initial dissolution stage of the active principle is slowed down to such an extent as to control the absorption of the active substance. The operation of some of these systems is influenced considerably by the hydrodynamic conditions of the environment into which the system is inserted (stomach, intestine etc.). Moreover, in the case of many of them the quantity of substance in the deposit has to be oversized relative to requirements because its release is incomplete.

Those implementations involving the release of medicaments which are poorly soluble in water or in biological fluids are also completely inadequate, and there also remains unsolved the problem of simultaneously releasing from a single system two or more active substances of different solubility, for which simultaneous transfer at equal or different rates is required.

An example of systems of the known art is described in Japanese patent application No. 065688 of 15.4.83.

The drawbacks encountered with systems of the known art are obviated by the system according to the present invention, which also has the advantage of allowing controlled-rate release, in particle form, of substances practically insoluble in water.

This system is based on controlling the release of the active substances by the swelling which the deposit-core containing it undergoes when it comes into contact with water or with aqueous liquids.

The system for the controlled-rate release of active substances according to the present invention consists of:

(a) a deposit-core comprising the active substance and having defined geometric form,
(b) a support-platform applied to said deposit-core,
and is characterised in that said deposit-core contains, mixed with the active substance, a polymeric material having a high degree of swelling on contact with water or aqueous liquids, a gellable polymeric material, said polymeric materials being replaceable by a single polymeric material having both swelling and gelling properties, and other adjuvants able to provide the mixture with suitable characteristics for its compression and for its intake of water, said support-platform consisting of a polymeric material insoluble in aqueous liquids and partially coating said deposit-core.

These and further characteristics and advantages of the system according to the invention will be more apparent from the detailed description of preferred embodiments of the invention given hereinafter by way of non-limiting example. The deposit-core is generally obtained by compressing the mixture containing the active substance to a pressure of between 1000 and 4000 kg/cm$^2$, to thus assume a defined geometric form.

Polymeric materials having a high degree of swelling are essentially generally cross-linked insoluble polymers, whereas gellable polymeric materials are soluble, their purpose being to control the intake of water.

Polymers having a high degree of swelling comprise, inter alia, cross-linked sodium carboxymethylcellulose, cross-linked hydroxypropylcellulose, high-molecular weight hydroxymethylpropylcellulose, carboxymethylamide, potassium methacrylatedivinylbenzene copolymer, polymethylmethacrylate, cross-linked polyvinylpyrrolidone, high-molecular weight polyvinylalcohols etc. Gellable polymers include methylcellulose, carboxymethylcellulose, low-molecular weight hydroxypropylmethylcellulose, low-molecular weight polyvinylalcohols, polyoxyethyleneglycols, non-cross linked polyvinylpyrrolidone etc. Polymers simultaneously possessing swelling and gelling properties include medium-viscosity hydroxypropylmethylcellulose and medium-viscosity polyvinylalcohols.

The coating platform consists of a polymeric material insoluble in water and in possibly biodegradable biological liquids, and able to maintain its impermeability characteristics at least until the complete transfer of the active substance contained in the deposit-core. It is applied to a part of the external deposit-core surface chosen such as to suitably direct and quantitatively regulate the release of the active substance. In this respect, as the support-platform is impermeable to water, the polymeric material of the deposit-core can swell only in that portion of the deposit not coated with the platform.

The support-platform can be obtained by compressing prechosen polymeric materials onto the deposit-core, by immersing the deposit-core in a solution of said polymeric materials in normal organic solvents, or by spraying said solutions. Polymeric materials usable for preparing the support-platform can be chosen from the class comprising acrylates, celluloses and derivatives such as ethylcellulose, cellulose acetate-propionate, polyethylenes and methacrylates and copolymers of acrylic acid, polyvinylalcohols etc.

This platform can have a thickness of between 2 mm if applied by compression and 10 microns if applied by spraying or immersion, and comprises from 10 to 90% of the total surface of the system.

The primary factor in controlling the release of the active substance is the intensity and duration of the swelling force developed by the swellable polymeric materials contained in the deposit-core on contact with aqueous fluids. In this respect, the energy for activating, executing and regulating the release of the active substance is determined by the swelling force developed in the deposit-core when this comes into contact with water or with biological liquids. Said force has an intensity and duration which vary in relation to the type and quantity of the polymeric materials used in formulating the deposit, and it lies between limits having a maximum value which occurs in the case of a deposit mainly containing the swellable polymer, and a minimum value which occurs in the case of a deposit mainly containing the gellable polymer.

Said swellable polymer is present to the extent of between 5 and 80% by weight, and said gellable polymer to the extent of between 90 and 10% by weight, with respect to the mixture forming the deposit-core.

A further control factor is the geometry of the support-platform, which limits the swelling of the deposit and directs the emission of material from it.

Within the scope of the present invention it is possible to conceive many systems for the controlled release of active substances, which base their operation on the swelling force and differ from each other by the type of support-platform used.

BRIEF DESCRIPTION OF THE DRAWING

Some embodiments are described by way of non-limiting example hereinafter, and their morphology and operation are illustrated in detail in the relative examples.

1st case: system with one flat, concave or convex support-platform.

In its simplest form, the system consists of:
(a) a deposit-core obtained by compression and containing the active principle and the swellable and gellable polymeric materials together with other components for making the mixture more easily compressible or for regulating water intake.

This deposit-core can generally have a geometric form similar to a cylindrical tablet with flat, convex or concave faces;
(b) a support-platform obtained by coating a base of the deposit-core with a layer of polymeric material, or a polymeric material mixture, which is inert and insoluble in the medium into which the active substance is to be transferred.

The control factor is the deposit-core composition (weight ratio of swellable to gellable polymers), which is chosen in such a manner as to obtain the desired swelling and thus the desired transfer rate of active substance. The platform limits the swelling of the deposit and directs the emission of active substance practically through 180°.

The structure of the system when dry, after hydration and when spent is shown in FIGS. 1, 2 and 3 respectively.

On contact with water or aqueous liquids, the system offers a large transfer surface, and for this reason is suitable for poorly soluble/soluble medicaments (water solubility between 1 g/liter and 33 g/liter).

2nd case: system with two parallel flat or concave support-platforms.

In its simplest form, the system consists of:
(a) a deposit-core obtained as described for the 1st case;
(b) a support-platform obtained by coating the two bases of the deposit with a layer of polymeric material, or a polymeric material mixture, which is inert and insoluble in the medium into which the active substance is to be transferred.

The control factor is the deposit-core composition (weight ratio of swellable to gellable polymers).

The platform limits the swelling of the deposit, and directs the emission of active substance practically in a radial direction.

The structure of the system when dry, after hydration and when spent is shown in FIGS. 4, 5 and 6 respectively.

On contact with water or aqueous liquids, the system offers a small transfer surface, and for this reason is suitable for soluble/very soluble medicaments (water solubility between 5 g/liter and 1000 g/liter).

3rd case: system with a container-shaped support-platform.

In its simplest form, the system consists of:
(a) a deposit-core obtained as described for the 1st case;
(b) a support-platform obtained by coating one base and the lateral surface of the deposit with a layer of polymeric material, or a polymeric material mixture, which is inert and insoluble in the medium into which the active substance is to be transferred.

The control factor is the deposit composition (weight ratio of swellable to gellable polymers). The platform limits the swelling of the deposit, and directs the emission of active substance practically in a direction perpendicular to the platform base.

The structure of the system when dry, after hydration and when spent is shown in FIGS. 7, 8 and 9 respectively On contact with water or aqueous liquids, the system offers a constant transfer surface. The system is suitable for practically insoluble, poorly soluble and very soluble medicaments (water solubility between 0.01 g/liter and 1000 g/liter).

A system of this latter type having a deposit consisitng of 78% of swellable polymer and 13% of gellable polymer develops the swelling force given in column (a) of Table I.

The same system but with a deposit consistng of 30% of a both swellable and gellable polymer develops the swelling force given in column (b) of Table I.

TABLE I

| Time (hours) | Swelling force (N) | |
| --- | --- | --- |
| | a | b |
| 0.5 | 39 | 12 |
| 1 | 30 | 10 |

TABLE I-continued

| Time (hours) | Swelling force (N) a | b |
|---|---|---|
| 2 | 20 | 5 |
| 4 | 8 | 0.6 |

4th case: system with a support-platform which laterally surrounds it.

In its simplest form, the system consists of:
(a) a deposit-core obtained as described for the 1st case;
A particular case is that of a deposit of cylindrical or other geometric form composed of two portions obtained by double compression, in which the upper portion contains one medicament and the lower portion contains another.
(b) a support-platform obtained by coating the lateral surface of the deposit with a layer of polymeric material, or a polymeric material mixture, which is inert and insoluble in the medium into which the active substance is to be transferred.

The control factor is the deposit-core composition (weight ratio of swellable to gellable polymers). The platform limits the swelling of the deposit, and directs the emission of active substance or of the two active substances in two opposing directions.

The structure of the system when dry, after hydration and when spent is shown in FIGS. 10, 11 and 12 respectively.

On contact with water or aqueous liquids, the system offers a large transfer surface, and for this reason is suitable for poorly soluble/soluble medicaments (water solubility between 0.1 g/liter and 100 g/liter) or for the simultaneous transfer of two different medicaments at the same rate or at different rates.

5th case: system with a support-platform covering one half of its surface

In its simplest form, the system consists of:
(a) a deposit-core obtained as described for the 1st case;
(b) a support-platform obtained by coating one half of the deposit surface with a layer of polymeric material, or a polymeric material mixture, which is inert and insoluble in the medium into which the active substance is to be transferred.

The control factor is the deposit-core composition (weight ratio of swellable to gellable polymers).

The platform limits the swelling to one half of the deposit.

The structure of the system when dry, after hydration and when spent is shown in FIGS. 13, 14 and 15 respectively.

On contact with water or aqueous liquids, the system offers a large transfer surface in the uncoated portion and a more limited transfer surface in the coated portion, and for this reason is suitable for medicaments which require high initial release followed by slower release.

EXAMPLE 1

Preparation of therapeutic systems in accordance with the procedures described for the 1st and 2nd cases.
a—Preparation of the deposit-core.
1000 deposit-cores were prepared using the following materials in the stated quantities:

| diltiazem | 45.0 g |
|---|---|
| hydroxypropylmethylcellulose | 35.0 g |

| (methocel K 100M-Colorcon) | |
|---|---|
| mannitol | 10.0 g |
| ethylcellulose (high viscosity-BDH) | 3.75 g |
| magnesium stearate | 1.0 g |
| 5:1 95° ethanol-chloroform mixture | 75.0 ml |

The diltiazem was mixed intimately with the mannitol and hydroxypropylmethylcellulose in a suitable mixer. The solution of ethylcellulose in ethanol-chloroform was prepared separately, and was used for wetting the previously obtained powder mixture. The resultant homogeneous mass was forced through an 800 micron screen and then dried to obtain a granulate which was passed through a 420 micron screen. The homogeneous granulate obtained was mixed with the magnesium stearate and then compressed using concave punches of diameter 7 mm (radius of curvature 9 mm) using a pressure of about 3000 kg/cm$^2$ to obtain cylindrical deposit-cores with convex bases.

b—Application of the support-platform.

The support-platform was applied by coating one or both the convex bases of the deposit-core with a solution of:

| low-permeability acrylic-methacrylic copolymer (eudragit RS Rohm Pharma) | 15 g |
|---|---|
| in methylene chloride of a quantity to make up to | 100 ml |

0.3 ml of said solution were applied to each base to be covered, taking care to protect the lateral core surface. The system was then dried with tepid air. The quantity of polymeric material deposited was sufficient to keep the structure intact during transfer.

c—"In vitro" transfer of the active principle.

The "in vitro" transfer tests were carried out both on the deposit-core (uncoated) and on the therapeutic systems complete with their support-platform. For this type of test, the USP XXI basket dissolving apparatus was used, the transfer fluid being 1000 ml of distilled water at 37° C.

The following results were obtained:
transfer of diltiazem from the deposit-core (uncoated)

| time (min) | cumulative fraction transferred |
|---|---|
| 30 | 0.27 |
| 60 | 0.39 |
| 120 | 0.57 |
| 180 | 0.72 |
| 240 | 0.83 | transfer of diltiazem from the deposit anchored to one concave platform (1st case)

| time (min) | cumulative fraction transferred |
|---|---|
| 30 | 0.22 |
| 60 | 0.34 |
| 120 | 0.51 |
| 180 | 0.66 |
| 240 | 0.77 |
| 360 | 0.94 | transfer of diltiazem from the deposit anchored to two parallel platforms (2nd case)

| time (min) | cumulative fraction transferred |
|---|---|
| 60 | 0.25 |
| 120 | 0.41 |
| 180 | 0.56 |
| 240 | 0.68 |
| 300 | 0.78 |
| 360 | 0.86 |

The release kinetics expressed by the equation:

fraction released = $K \times$ (time)$^n$ were as follows:

| | |
|---|---|
| deposit-core: | fraction released = 0.48 × (time)$^{0.51}$ |
| system of 1st case: | fraction released = 0.32 × (time)$^{0.57}$ |
| system of 2nd case: | fraction released = 0.012 × (time)$^{0.71}$ |

EXAMPLE 2

Preparation of therapeutic systems by the procedures described for the 3rd case.

a—Preparation of the deposit-core.

1000 deposit-cores were prepared using the following materials in the stated quantities:

| | |
|---|---|
| nifedipine | 20 g |
| sodium carboxymethylcellulose (ACDISOL-FMC) | 180 g |
| hydroxypropylmethylcellulose (methocel K4M-Colorcon) | 30 g |
| magnesium stearate | 1 g |

The nifedipine was mixed with acdisol for 30 minutes in a suitable mixer, methocel K4M and magnesium stearate were added, and mixing was continued for a further 30 minutes. Tablets (diameter 20 mm) were obtained by compression, and were then ground in a swinging arm granulator to obtain a granulate which passed through a 600 micron screen. The granulate obtained was compressed by punches of diameter 9.5 mm to a pressure of 3000 kg/cm$^2$ to obtain cylindrical deposit-cores.

b—Application of the support-platform.

The platform was applied by coating one base and the lateral surface of the cylindrical deposit with a solution of:

| | | |
|---|---|---|
| cellulose acetate propionate (CAP 482-20 Eastman-Kodak) | 15 | g |
| castor oil | 1 | g |
| acetone | 100 | ml |

The deposit-core was immersed in a polymeric solution as far as the edge of its upper base, and was then dried in a stream of tepid air. The quantity of solution applied was 1.5 ml.

c—"In vitro" transfer of the active principle.

The "in vitro" transfer tests were carried out with the continuous-flow SOITAX (CH) dissolving apparatus, operating with distilled water at 37° at a throughput of 17 ml/min.

The following results were obtained:
transfer fo nifedipine from the system

| time (min) | cumulative fraction transferred |
|---|---|
| 60 | 0.091 |
| 120 | 0.180 |
| 180 | 0.260 |
| 300 | 0.440 |
| 360 | 0.520 |

The release kinetics are expressed by the zero-order equation:

fraction released = 0.0014 × time + 0.0053.

EXAMPLE 3

Preparation of therapeutic systems by the procedure described for the 4th case.

a—Preparation of the deposit-core.

1000 deposit-cores were prepared using the following materials in the stated quantities:

| | | |
|---|---|---|
| Blue granulate | | |
| diazepam | 5 | g |
| anhydrous citric acid | 10 | g |
| mannitol | 77.75 | g |
| methocel K4M | 7.5 | g |
| methocel K15M | 7.5 | g |
| polyvinylpyrrolidone | 2 | g |
| blue colouring (FCD n 3) | 0.25 | g |
| magnesium stearate | 1 | g |
| 95° ethanol | 40 | ml |
| White granulate | | |
| octatropine methylbromide | 60 | g |
| mannitol | 33 | g |
| methocel K4M | 7.5 | g |
| methocel K15M | 7.5 | g |
| polyvinylpyrrolidone | 2 | g |
| magnesium stearate | 1 | g |
| 95° ethanol | 40 | ml |

The two granulates were prepared in an analogous manner by the folllowing procedure: the polyvinylpyrrolidone was dissolved in the ethanol whereas the other components, with the exception of the magnesium stearate, were mixed together intimately. The powder mixture was mixed with the polyvinylpyrrolidone solution and forced through a 600 micron screen, the obtained granules being mixed with the magnesium stearate after drying. Two granulates were thus produced, one white and one blue. The two granulates were poured separately into the hoppers of a compressing machine for double-layer tablets and compressed to 3000 kg/cm$^2$ with 7 mm diameter punches to obtain a type of deposit-core of cylindrical form with two superimposed coloured layers.

b—Application of the support-platform.

The platform was applied by coating the lateral surface of the cylindrical deposit with a solution of:

| | | |
|---|---|---|
| acrylic-methacrylic copolymer (eudragit RS) | 24 | g |
| castor oil | 1 | g |
| acetone | 50 | ml |
| isopropanol | 50 | ml |

The deposit-core was coated on its lateral surface by spraying or brushing the polymeric solution, which was then dried in a stream of tepid air. The quantity of solution applied was 0.7 ml.

c—"In vitro" transfer of the active principle.

The "in vitro" transfer tests were carried out with the USP XXI basket dissolving apparatus, operating in 1000 ml of distilled water at 37° C. at a rotation speed of 150 rpm.

The following results were obtained:
transfer of octatropine methyl bromide and diazepam from the system.

| time (min) | cumulative fraction transferred | |
| --- | --- | --- |
|  | octatropine | diazepam |
| 30 | 0.13 | 0.12 |
| 60 | 0.24 | 0.23 |
| 120 | 0.41 | 0.33 |
| 180 | 0.56 | 0.51 |
| 240 | 0.70 | 0.62 |

The release kinetics, expressed by the equation:

$$\text{fraction released} = K \times (\text{time})^n$$

were as follows:

| | |
| --- | --- |
| diazepam | fraction released = $0.012 \times (\text{time})^{0.71}$ |
| octatropine | fraction released = $0.011 \times (\text{time})^{0.76}$ |

We claim:

1. A system for the controlled-rate release of active substances, consisting of:
   (a) a deposit-core comprising effective amounts of the active substances and having defined geometric form,
   (b) a support-platform applied to said deposit-core wherein said deposit-core contains, mixed with the active substance,
   at least one member selected from the group consisting of (a) 5–80% by weight of the total weight of the deposit-core of a polymeric material having a high degree of swelling on contact with water or aqueous liquids and 90–10% by weight of the total weight of the deposit core of a gellable polymeric material, and (b) a single polymeric material having both swelling and gelling properties, and
   other adjuvants able to provide the mixture with suitable characteristics for compression and for intake of water,
   and wherein said support-platform consists of a polymeric material insoluble in aqueous liquids and partially coating said deposit-core.

2. A system as claimed in claim 1, characterised in that said deposit-core is obtained by compressing said mixture to a pressure of between 1000 and 4000 kg/cm$^2$.

3. A system as claimed in claim 1, characterised in that said polymeric material with a high degree of swelling comprises at least one member selected from the group consisting of cross-linked sodium carboxymethylcellulose, cross-linked hydroxypropylcellulose, high-molecular weight hydroxypropylmethylcellulose, carboxymethylamide, potassium methacrylatedivinylbenzene copolymer, polymethylmethacrylate, cross-linked polyvinylpyrrolidone and high-molecular weight polyvinylalcohols.

4. A system as claimed in claim 1, characterised in that said gellable polymeric material comprises at least one member selected from the group consisting of methylcellulose, carboxymethylcellulose, low-molecular weight hydroxypropylmethylcellulose, low-molecular weight polyvinylalcohols, polyoxyethyleneglycols and non-cross linked polyvinylpyrrolidone.

5. A system as claimed in claim 1, characterised in that said polymeric material with swelling and gelling properties comprises at least one member selected from the group consisting of medium-viscosity hydroxypropylmethylcellulose and medium-viscosity polyvinylalcohols.

6. A system as claimed in claim 1, characterised in that said support-platform covers one half of the surface of said deposit-core.

7. A system as claimed in claim 1, characterised in that said support-platform is formed by applying said water-insoluble polymeric material to said deposit-core by compression.

8. A system as claimed in claim 1, characterised in that said support-platform is formed by immersing said deposit-core in a solution of said water-insoluble polymeric material in a organic solvent.

9. A system as claimed in claim 1, characterised in that said support-platform is formed by spraying said water-insoluble polymeric material in the form of a solution in an organic solvent onto said deposit-core.

10. A system as claimed in claim 1, characterised in that said support-platform has a thickness of between 10 microns and 2 mm.

11. A system as claimed in claim 1, characterised in that said support-platform covers from 10 to 90% of the total surface of the system.

12. A system as claimed in claim 1, characterised in that said polymeric material insoluble in aqueous liquids comprises at least one member selected from the group consisting of acrylates, cellulose, ethylcellulose, cellulose acetate-propionate, polyethylene, methacrylates, acrylic acid copolymers and high-molecular weight polyvinylalcohols.

13. A system as claimed in claim 1, characterised in that the intensity and duration of the swelling force of said polymeric material with a high degree of swelling constitutes the primary control factor for the release of the active substance.

14. A system as claimed in claim 1, characterised in that the geometry of said support-platform constitutes a further control factor for the release of the active substance and directs the emission thereof.

15. A system as claimed in claim 1, characterised in that said adjuvants are magnesium stearate and mannitol.

16. A system as claimed in claim 1, characterised in that said deposit-core is formed from two layers, each of which comprises an active substance, a polymeric material with a high degree of swelling, and a gellable polymeric material.

17. A system as claimed in claim 1, characterised in that said support-platform is in the form of a coating applied to one flat, convex or concave surface of said deposit-core.

18. A system as claimed in claim 1, characterised in that said support-platform is in the form of a coating applied to two separate zones of the surface of said deposit-core.

19. A system as claimed in claim 1, characterised in that said support-platform is in the form of a coating which surrounds said deposit-core, to leave two opposing surface portions free.

20. A system as claimed in claim 1, characterised in that said support-platform is in the form of a container which encases said deposit-core, to leave one surface portion free.

21. A therapeutic system having a form and structure suitable for administration to a patient, wherein said system comprises a dosage unit consisting of a number of systems as claimed in claim 1 disposed in one container.

22. A method for preparing a system claimed in claim 1, characterised in that the mixture containing the active substance and the polymeric materials is wetted with a solution of adjuvants to obtain a granulate which is compressed to obtain the deposit-core, which is then coated over a determined area with a water-insoluble polymeric material possibly dissolved in an organic solvent.

23. A system for the controlled-rate release of active substances, consisting of:
(a) a deposit-core comprising effective amounts of the active substances and having defined geometric form,
(b) a support-platform applied to said deposit-core wherein said deposit-core contains, mixed with the active substance,
   at least one member selected from the group consisting of (a) 5–80% by weight of the total weight of the deposit-core of at least one polymeric material having a high degree of swelling on contact with water or aqueous liquids selected from the group consisting of cross-linked sodium carboxymethylcellulose, cross-linked hydroxypropylcellulose, high-molecular weight hydroxypropylmethylcellulose, carboxymethylamide, potassium methacrylatedivinylbenzene copolymer, polymethylmethacrylate, cross-linked polyvinylpyrrolidone, and high-molecular weight polyvinylalcohols; and 90–10% by weight of the total weight of the deposit-core of at least one gellable polymeric material selected from the group consisting of methylcellulose, carboxymethylcellulose, low-molecular weight hydroxypropylmethylcellulose, low-molecular weight polyvinylalcohols, polyoxyethyleneglycols and non-cross linked polyvinylpyrrolidone; and (b) a single polymeric material having both swelling and gelling properties selected from the group consisting of medium-viscosity hydroxypropylmethylcellulose and medium-viscosity polyvinylalcohols; and other adjuvants able to provide the mixture with suitable characteristics for compression and for intake of water, and wherein said support-platform consists of a polymeric material insoluble in aqueous liquids and partially coating said deposit-core.

24. A system as claimed in claim 23, wherein said deposit-core contains said polymeric material having a high degree of swelling and said gellable polymeric material.

25. A system as claimed in claim 23, wherein said deposit-core contains said single polymeric material having both swelling and gelling properties.

* * * * *